United States Patent [19]

Weigert

[11] Patent Number: 5,093,527
[45] Date of Patent: Mar. 3, 1992

[54] PROCESS FOR PREPARING METHYL- AND ETHYL-SUBSTITUTED PRIMARY ANILINES

[75] Inventor: Frank J. Weigert, Wilmington, Del.

[73] Assignee: E. I. Du Pont de Nemours and Company, Wilmington, Del.

[21] Appl. No.: 782,575

[22] Filed: Oct. 1, 1985

Related U.S. Application Data

[62] Division of Ser. No. 559,184, Dec. 7, 1983, abandoned.

[51] Int. Cl.$^5$ .................. C07C 209/00; C07C 211/47; C07C 211/45
[52] U.S. Cl. .................................................... 564/409
[58] Field of Search ........................................ 564/409

[56] References Cited

U.S. PATENT DOCUMENTS

| | | | |
|---|---|---|---|
| 3,123,644 | 3/1964 | Olin | 564/409 |
| 3,868,420 | 2/1975 | Evans et al. | 260/576 |
| 3,931,298 | 1/1975 | Wollensak | 260/581 |
| 3,960,962 | 6/1976 | Shubkin | 260/581 |
| 4,188,341 | 2/1980 | Fischer | 260/573 |
| 4,593,124 | 6/1986 | Weigert | 564/409 |

FOREIGN PATENT DOCUMENTS

| | | |
|---|---|---|
| 0092103 | 4/1982 | European Pat. Off. |
| 29178 | 8/1974 | Japan |
| 53-28128 | 3/1978 | Japan |
| 28129 | 3/1978 | Japan |

OTHER PUBLICATIONS

Matsumoto, Chemistry Letters, pp. 939 to 942 (1977).
M. Inoue and S. Enomoto, Sekiyu Gakkaishi, 15, 372 to 378 (1972).
Matsumoto et al., Chemistry Letters, pp. 435–438 (1978).

Primary Examiner—Carolyn Elmore
Attorney, Agent, or Firm—James A. Costello

[57] ABSTRACT

A process is disclosed for the preparation of methyl- and ethyl-substituted anilines by contacting anilines of specified formula at about 250°–525° C. and about 10 kPa–10 MPa of pressure in the of presence of a nonbasic metal oxide catalyst which when it is a zeolite has pore dimensions of at least about 0.52 nm and has cages with dimensions greater than about 0.75 nm.

4 Claims, 1 Drawing Sheet

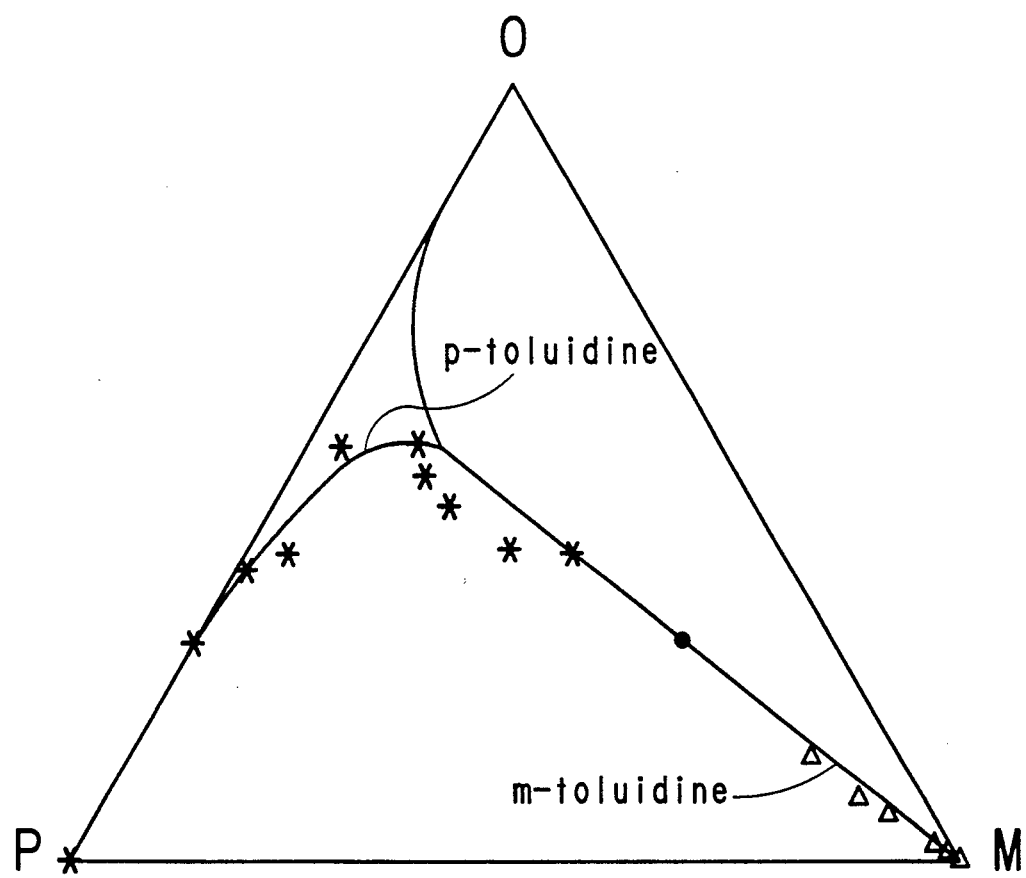

PROCESS FOR PREPARING METHYL- AND ETHYL-SUBSTITUTED PRIMARY ANILINES

CROSS-REFERENCE TO RELATED APPLICATION

This application is a division of application Ser. No. 559,184, filed Dec. 7, 1983, now abandoned.

BACKGROUND OF THE INVENTION

This invention relates to a process for the preparation of methyl- and ethyl-substituted anilines.

Methyl-substituted anilines are useful in a variety of applications such as in the preparation of dyes, herbicides, insecticides, plant growth agents and antiknock agents for gasoline engines. The anilines are generally prepared by nitration of the appropriate methyl benzene followed by reduction of the resulting nitro compound. This process depends upon the availability of the appropriate nitro compound which in some instances is unavailable or available only in limited quantities. For example, m-toluidine is important as an intermediate in dyes and agricultural chemicals. However, in the foregoing nitration-reduction process, only 4% of the toluidines produced are m-toluidine. As a result, separation of m-toluidine is a complex process and consequently the meta-isomer is the most expensive of the toluidines.

U.S. Pat. No. 3,868,420, issued to Evans et al. on Feb. 25, 1975, discloses a process for producing phenylamines alkylated in the ortho and/or para positions by alkyl groups of 1-4 carbon atoms and unsubstituted on the amino group which comprises reacting a suitable phenylamine with an alkanol of 1-4 carbon atoms in the vapor phase at a temperature of from 350° to 450° C. in the presence of an aluminum oxide catalyst or an aluminum oxide/molybdenum oxide mixed catalyst, said catalyst having a minimum surface area of 50 m²/g. U.S. Pat. No. 3,931,298, issued to Wollensak on Jan. 6, 1976, discloses a process for converting hydroxy-substituted aromatic compounds to the corresponding amine by reacting the aromatic hydroxy compound with ammonia in the presence of a catalytic amount of a cyclohexane and in contact with a hydrogen-transfer catalyst, most preferably palladium. U.S. Pat. No. 3,960,962, issued to Shubkin on June 1, 1976, discloses a similar process wherein the catalyst comprises metallic palladium bonded to a phosphinated polystyrene resin.

U.S. Pat. No. 4,188,341, issued to Fischer on Feb. 12, 1980, discloses a process for making 2,6-dimethylaniline or an N-substituted 2,6-dimethylaniline comprising reacting an enamine of a specified formula at a temperature of between $-30°$ C. and 150° C. with acrolein in the presence of an inert aprotic solvent and heating the resulting reaction product to a temperature of between 100° and 400° C. in the presence of a hydrogen-transfer catalyst and an amine of the formula $RNH_2$ wherein R is —H or a specified lower alkyl.

Japanese Patent Application Publication Kokai No. 53-28128 discloses a process for para-methylation of anilines comprising reacting an aniline having para-hydrogens with methanol in the presence of an alkali metal synthetic zeolite catalyst, particularly NaY zeolite. Preparation of 2,4-dimethylaniline from o-toluidine and the preparation of p-toluidine from aniline are specifically disclosed.

T. Matsumoto, Chemistry Letters, p. 939 (1977), discloses the ortho-methylation of 2,3-dimethylaniline with methanol over various solid catalysts with 5 wt % Ag on $Al_2O_3$ showing the highest selectivity to ortho-methylation, that is, the production of 2,3,6-trimethylaniline. M. Inoue and S. Enomoto, Sekiyu Gakkaishi, 15, 372 (1972) studied the methylation of aromatic compounds with methanol in vapor or liquid phase on various catalysts and specifically report the ortho-methylation of aniline with methanol using 10% $MgO/Al_2O_3$ catalyst to produce o-toluidine.

Japanese Patent Publication 28129/1978 discloses demethylation of polymethylanilines, which contain at least more than two methyl groups, in the presence of a catalyst composition of the formula $A_aB_bC_cO_d$ wherein A is titanium; B represents more than one kind of element selected from zinc, zirconium and magnesium; C represents more than one kind of element, selected from vanadium, chromium, manganese, tin, iron, cobalt, nickel, copper, molybdenum, tungsten, barium, calcium; O is oxygen; a is 1, b is 0.05 to about 20, and c is 0 to 1.0. Reaction temperatures of 440°-600° C. are disclosed. Ti—Zr catalyst systems are stated to give mainly p-demethylated products, such as 2,6-xylidine from mesidine. Ti—Zn or Mg catalyst systems give o- and/or p-demethylated products, such as m-toluidine from 2,3-, 3,4-, and 2,5-dimethylaniline, 2,4,5-trimethylaniline; and 2,3,4,6-tetramethylaniline.

Japanese Patent Publication No. 1974-[Showa -49], 29,178 discloses a process for the synthesis of toluidines rich in m-toluidine by dealkylation of xylidines having a methyl group in a meta position at 400°-700° C. in the presence of a dealkylation catalyst such as silica-alumina, alumina, silica, silica-magnesia and magnesia. Matsumoto et al., Chemistry Letters, pp 435-438 (1978) disclose a process for preparing m-toluidine by hydrocracking 2,3-xylidine over metal oxide-supported nickel catalysts. The authors disclose that the selectivity of m-toluidine is influenced by side reactions, such as isomerization, and that the extent of isomerization can be related to the acidic character of the metal oxide carriers.

SUMMARY OF THE INVENTION

The present invention provides a process for preparing one or more substituted anilines of the formula

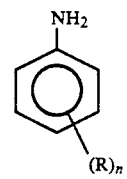

wherein R is —$CH_3$ or —$C_2H_5$ and n is 1 or 2 comprising contacting an aniline of the formula

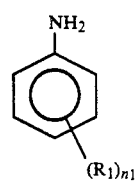

with an aniline of the formula

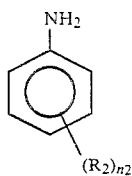

wherein $R_1$ and $R_2$ are both methyl or ethyl, $n_1$ and $n_2$ are different and are individually an integer from 0 to 3, and $n_1+n_2$ is an integer from 1 to 5, said contacting being performed in the presence of a nonbasic metal oxide catalyst at a temperature of from about 250° to about 525° C. and at a pressure of from about 10 kPa to about 10 MPa, the formula I product being different from the formulae II and III starting materials and the total number of R groups attached to the resulting products being equal to the total number of R groups attached to the starting aniline; with the proviso that when the nonbasic metal oxide catalyst is a zeolite it has pore dimensions of at least about 0.52 nm and has cages with dimensions greater than about 0.75 nm.

BRIEF DESCRIPTION OF THE DRAWING

The FIGURE shows the kinetic paths followed by m- and p-toluidines in the presence of aniline to reach equilibrium when equilibration takes place over HY zeolite.

DETAILED DESCRIPTION OF THE INVENTION

Transmethylation is represented by the reaction

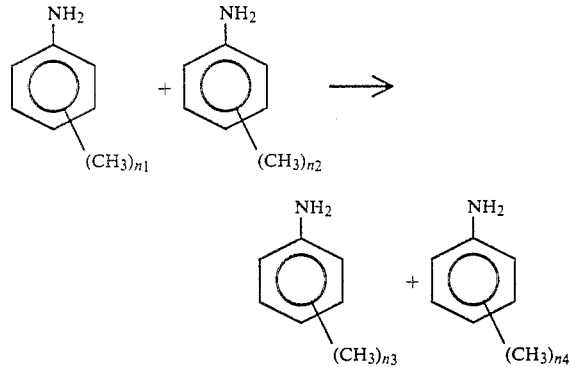

where $n_1$, $n_2$, $n_3$, and $n_4$ represent the number of methyl groups on each aniline and $n_1+n_2$ is an integer from 1 to 5 with the proviso that $n_1$ and $n_2$ are different and are individually an integer from 0 to 3 and $n_1+n_2$ equals $n_3+n_4$. The product can contain one or more isomers corresponding to a given number of methyl groups.

Transethylation proceeds in a similar manner.

The process of the invention includes (a) the production of toluidine and dimethylaniline from aniline and 2,4,6-trimethylaniline:

(b) the production of dimethylanilines from toluidine and 2,4,6-trimethylaniline:

(c) the production of toluidines from dimethylanilines and aniline: and (d) the production of isomers of a dimethylaniline and of a toluidine.

Catalysts suitable for the present process include molecular sieves, i.e., type X and Y zeolites, silica, alumina, silica-alumina compositions, titania, zirconia, iron oxide, zinc oxide and Group V and VI metal oxides. Molecular sieves are commercially available as are many of the other suitable catalysts. Metal oxide catalyst compositions for use as catalysts in the present invention can be prepared by impregnating a substrate with a solution(s) containing the desired oxide(s), co-precipitating the desired materials on the substrate or by evaporation or spattering techniques well known in the art. When the catalyst is other than a molecular sieve it is preferably amorphous.

When the nonbasic metal oxide is a zeolite (molecular sieve) it has pore dimensions of at least about 0.52 nm and has cages with dimensions greater than about 0.75 nm. One skilled in the art will recognize that as the number of methyl or ethyl groups on the reactants increases, the minimum pore and cage dimensions must increase correspondingly. The zeolites X and Y are suitable in general for the transalkylation process of the invention. As used herein pore dimensions mean the aperture dimensions determined from crystal structure analyses, i.e., the crystallographic free diameters of the channels as discussed by W. M. Meier and D. H. Olson, "Atlas of Zeolite Structure Types", published by the Structure Commision of the International Zeolite Associations, 1978. The free diameter values are based on the atomic conditions of the type species in the hydrated state and an oxygen radius of 1.35 Å (0.135 nm).

In the process of the invention, the total number of methyl or ethyl groups on the primary anilines is substantially conserved. Minor portions of one or more reactants may undergo reactions in which some of the methyl or ethyl groups are lost by the anilines. However, except at the highest temperatures, the major portions of the reactants undergo the foregoing transalkylation reaction in which the number of methyl or ethyl groups on the reactant anilines equals the number on the product anilines.

The efficiency of a particular transalkylation is determined by the two substituted aniline reactants and the catalyst. The ease of the reaction increases as the sum of $n_1+n_2$ increases from one to five. Nonbasic oxides can catalyze the transalkylation of aniline and 2,4,6-trimethylaniline (TMA). Acidic oxides, but not neutral ones, catalyze transalkylations where $n_1+n_2=2$ but strong acids, such as the hydrogen-exchanged Y zeolite (HY) and other silica-alumina compositions, are required when $n_1+n_2=1$. A discussion of acidic strengths is contained in K. Tanabe, "Solid Acids and Bases". Academic Press, New York (1970).

A specific transmethylation is the reaction of aniline and 2,4,6-trimethylaniline over a nonbasic metal oxide catalyst to produce 2,4- and 2,6-dimethylaniline and o- and p-toluidine. The different metal oxide catalysts redistribute the methyl groups between 2,4,6-trimethylaniline and aniline differently and can be grouped according to the selectivity they show toward producing either 2,6-dimethylaniline and p-toluidine or 2,4-dimethylaniline and o-toluidine. In general, all four products are present to some degree and, in addition, there may also be small amounts of m-toluidine and other dimethylanilines.

Silica-aluminas show high selectivity to 2,6-dimethylaniline and p-toluidine, that is, to the transfer of the methyl from the para-position of 2,4,6-trimethylaniline to the para-position of aniline. The larger pore zeolites, such as zeolites X and Y, are examples of such catalysts, and the zeolite HY and the rare earth-exchanged X zeolite (REX) are especially preferred. Silica-alumina compositions include those ranging from pure silica to pure alumina.

In contrast, supported titania, zirconia, iron oxide, zinc oxide, and Group V and VI metal oxides show good selectivity to 2,4-dimethylaniline and o-toluidine, that is, to the transfer of the methyl from the ortho-position of 2,4,6-trimethylaniline to the ortho-position of aniline.

Each of these two groups of catalysts is more selective to the particular dimethylaniline and toluidine at lower operating temperatures and shorter contact times. In general, as the reaction conditions become increasingly severe, by raising the temperature and/or increasing the contact time, overall conversion is increased but selectivity to the particular dimethylaniline and toluidine is reduced. The process of the invention is conducted at a temperature of from about 250° to about 525° C., preferably from about 300° to 400° C., and at a pressure of from about 10 kPa (0.1 atmospheres) to about 10 MPa (100 atmospheres) for a period of time from about 0.1 sec to about 10 hours. The process of the invention can be carried out in either a liquid or gas phase. Times of about 1 sec and 0.5 hr will often be suitable for vapor phase and liquid phase reactions, respectively. Preferably, a pressure of about 1 atmosphere is used for vapor-phase reactions and autogenous pressure is used for liquid-phase reactions.

Some of the same metal oxides useful as a catalyst in the reaction of aniline and 2,4,6-trimethylaniline are also useful as a catalyst in the other transmethylation processes of this invention and in particular for the transmethylation represented by the reaction:

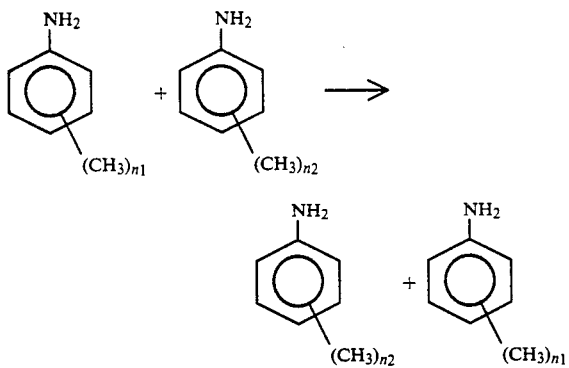

where the product aniline with $n_1$ is a different isomer than the reactant aniline with $n_1$ and the anilines with $n_2$ represent the same isomer. In essence, the aniline with $(CH_3)_{n2}$ is a co-catalyst for the isomerization of the aniline with $(CH_3)_{n1}$ creating a transmethylation process which in effect results in the equilibration of one of the reactants. For these equilibration processes useful catalysts are determined by the same rules concerning the sum of $n_1+n_2$ as set forth earlier herein.

Equilibration of 2,4- and 2,6-dimethylaniline occurs when one or both of these isomers is reacted with either o-toluidine or 2,4,6-trimethylaniline. The product can also contain some aniline, p- and m-toluidine and, when o-toluidine is a reactant, 2,4,6-trimethylaniline. Equilibration of 2,3-, 2,5-, and 3,4-dimethylanilines occurs when one or more of these isomers is reacted with m-toluidine. The product can also contain small amounts of 2,4- and 2,6-dimethylanilines.

Toluidine equilibration occurs when one or more toluidines are reacted with aniline. The ortho and para isomers are rapidly interconverted and the resulting two component equilibrium mix and the meta isomer then slowly approach the three component equilibrium (17% p-, 31% o-, and 52% m-toluidine). This equilibration in the presence of HY zeolite catalyst is the basis for the theoretical lines shown in the Figure. However, there are competing reactions. While a 10% solution of o-toluidine in aniline approximates the theoretical line shown in the Figure, a 1:1 mix of aniline and o-toluidine does not follow the curve, but bends toward the three component equilibrium much earlier, and pure o-toluidine proceeds almost straight to the three component equilibrium. The disproportionation of two o-toluidines to a dimethylaniline and aniline appears to be competitive with the reaction of o-toluidine and aniline to give p-toluidine and aniline, but can be controlled by working with an excess of aniline. For equilibration the co-catalyst should be present in an amount sufficient to ensure that the equilibration reaction dominates over reactions involving solely one of the reactants.

The invention is further illustrated by the following examples in which all temperatures are in degrees Celsius and all percentages are by weight unless otherwise stated.

EXAMPLE 1

A solution of equimolar amounts of aniline and 2,4,6-trimethylaniline was passed over 3 g of HY zeolite catalyst at atmospheric pressure and a temperature of 300°-400°, at a flow rate of 2 ml/hr with a nitrogen gas flow rate of 40 ml/min, in a 13 cm (5 inch) long - 1 cm (⅜ inch) diameter, heat resistant glass reactor heated with a split tube furnace. The HY zeolite used in this and later examples had a unit cell dimension of 24.45 Å, a $SiO_2/Al_2O_3$ ratio of 3.31, and a $Na_2O$ content of 0.15%. This process was continued for 30 minutes at a fixed reaction temperature, e.g., 300°, and the resulting liquid effluent collected. The foregoing steps were then repeated at temperatures of 350° and 400°. Each resulting product was analyzed by gas chromatography using a 6.1 m (20 ft) by 0.32 cm (⅛ inch) stainless steel column packed with polyethylene oxide of a molecular weight of about 20,000 and 1% KOH on 80/100 mesh diatomaceous earth. Elution was carried out isothermally at 200° with a nitrogen gas flow or 40 cc/minute. Retention times increase in the order aniline, ortho-, para- and meta-toluidine, 2,6- and 2,4-dimethylaniline (DMA) and 2,4,6-trimethylaniline (TMA). The results are summarized in Table I. Selectivity to 2,6-dimethylaniline (2,6-DMA) is defined as the percentage of DMA product that is 2,6-DMA, i.e., $$\frac{2,6\text{-DMA}}{2,6\text{-DMA} + 2,4\text{-DMA}} \times 100$$

where the quantities of 2,6-DMA and 2,4-DMA are in moles. The selectivity to p-toluidine is similarly defined as $$\frac{p\text{-toluidine}}{p\text{-toluidine} + o\text{-toluidine}} \times 100.$$

Likewise, 2,4,6-TMA conversion is defined as $$1 - \left( \frac{2,4,6\text{-TMA}}{2,4,6\text{-TMA} + 2,4\text{-DMA} + 2,6\text{-DMA} + \text{o-toluidine} + \text{p-toluidine}} \right) \times 100$$

The amount of m-toluidine and other DMA isomers in each product was negligible. As the reaction temperature increased, the conversion of 2,4,6-TMA increased; however, selectivity to 2,6-DMA and to p-toluidine decreased.

EXAMPLES 2-11

Aniline and 2,4,6-TMA were reacted over other silica-alumina catalysts that show high selectivity to 2,6-DMA and p-toluidine in a manner similar to that described in Example 1. The process conditions and results are summarized in Table I. In each example, 3 g of catalyst were used, reactor effluent obtained during the first 25 minutes of operation was discarded, and product obtained during the next 5 minutes of operation was collected and analyzed using gas chromatography. A 3.0 m (10 foot)×0.32 cm (⅛ inch) stainless steel column packed with 2% UCON 50 HB 5100 and 1.0% KOH on 80/100 mesh diatomaceous earth was used to characterize the product. A helium gas flow of 25 ml/min was used and elution was carried out at 150°. Elution of all peaks of interest took place within 14 minutes.

EXAMPLES 12-22

Aniline and 2,4,6-TMA were reacted over the titania, zirconia and other Group V and VI metal oxide catalysts which show good selectivity to 2,4-DMA and o-toluidine in a manner similar to that described for Examples 2-11 and the process conditions and results are summarized in Table I. Note that a low selectivity to 2,6-DMA and p-toluidine represents a correspondingly high selectivity to 2,4-DMA and o-toluidine, respectively.

EXAMPLES 23-26

In order to demonstrate liquid phase reaction of aniline and 2,4,6-TMA, 2 ml of an aniline-2,4,6-TMA solution and 0.5 g catalyst were placed in a shaker tube which was then evacuated at room temperature and sealed. The tube was heated to a desired reaction temperature, shaken for a given time, and was then cooled to room temperature. The contents of the tube were analyzed by gas chromatography using a procedure similar to that described in Examples 2-10. Process conditions are listed and results summarized in Table II.

EXAMPLES 27-29

The use of nonbasic metal oxide catalysts to equilibrate anilines by a transmethylation process was demonstrated in a manner similar to that used to demonstrate the transmethylation process described in Example 1. A solution of o-toluidine and 2,4- and/or 2,6-DMA was passed over 3 g of HY zeolite catalyst at atmospheric pressure and a given reaction temperature at a flow rate of 3 ml/hr with a nitrogen gas flow rate of 10 ml/min in a vapor phase reactor similar to that used in Example 1. Liquid effluent was collected and analyzed by gas chromatography using a procedure similar to that described in Examples 2-10. The process conditions used for each example and the results are summarized in Table III. The product can contain aniline, p- and m-toluidine, and 2,4,6-TMA in addition to the 2,4- and 2,6-DMA and o-toluidine.

TABLE I

| Example No. | Catalyst | Feed Ratio Aniline: 2,4,6-TMA (moles) | Feed Flow Rate ml/hr | N₂ Gas Flow ml/min | Reaction Temp (degrees) | Conversion of 2,4,6-TMA | Selectivity to 2,6-DMA | Selectivity to p-toluidine |
|---|---|---|---|---|---|---|---|---|
| 1 | HY Zeolite | 1 | 2 | 40 | 300 | 62 | 92 | 67 |
|  |  |  |  |  | 350 | 77 | 58 | 46 |
|  |  |  |  |  | 400 | 85 | 55 | 28 |
| 2 | 91% Al₂O₃/6% SiO₂ | 1 | 3 | 10 | 375 | 15 | 79 | 88 |
|  |  |  |  |  | 450 | 64 | 52 | 47 |
| 3 | 10% Al₂O₃/SiO₂ | 2 | 3 | 10 | 375 | 8 | 82 | 100 |
|  |  |  |  |  | 450 | 38 | 59 | 61 |
| 4 | 12% Al₂O₃/86% SiO₂ | 2 | 3 | 10 | 300 | 6 | 92 | 100 |
|  |  |  |  |  | 375 | 40 | 83 | 88 |
|  |  |  |  |  | 450 | 81 | 57 | 53 |
| 5 | Attapulgus Clay | 1 | 3 | 10 | 300 | 7 | 78 | 92 |
|  |  |  |  |  | 375 | 17 | 66 | 81 |
|  |  |  |  |  | 450 | 40 | 46 | 64 |
| 6 | Bentonite Clay | 2 | 3 | 10 | 300 | 30 | 86 | 91 |
|  |  |  |  |  | 375 | 29 | 71 | 82 |
|  |  |  |  |  | 450 | 39 | 48 | 60 |
| 7 | Kaolinite Clay | 2 | 3 | 10 | 450 | 15 | 50 | 65 |
| 8 | SiO₂ | 1 | 3 | 10 | 450 | 17 | 47 | 63 |
| 9 | 99% Al₂O₃ | 1 | 3 | 10 | 375 | 3 | 50 | 75 |
|  |  |  |  |  | 450 | 29 | 38 | 51 |
| 10 | HY Zeolite | 3.5 | 3 | 10 | 260 | 51 | 92 | 76 |
|  |  |  | 3 | 10 | 290 | 80 | 85 | 68 |
|  |  |  | 1.5 | 25 | 260 | 68 | 87 | 78 |
|  |  |  | 1.5 | 50 | 260 | 53 | 88 | 85 |
| 11 | REX Zeolite | 1 | 2 | 40 | 300 | 59 | 83 | Not measured |
|  |  |  |  |  | 350 | 73 | 60 |  |
| 12 | TiO₂ | 1 | 3 | 10 | 475 | 15 | 8 | 36 |
| 13 | ZrO₂ | 1 | 3 | 10 | 375 | 2 | 43 | 50 |
|  |  |  |  |  | 450 | 44 | 41 | 45 |
| 14 | 10% ZnO/TiO₂ | 1 | 3 | 10 | 450 | 17 | 8 | 30 |
| 15 | Sb/9Ti/O | 1 | 3 | 10 | 375 | 19 | 21 | 25 |
|  |  |  |  |  | 450 | 43 | 18 | 39 |
| 16 | 10% MoO₃/Al₂O₃ | 2 | 3 | 10 | 375 | 14 | 25 | 39 |
|  |  |  |  |  | 400 | 46 | 18 | 33 |

TABLE I-continued

| Example No. | Catalyst | Feed Ratio Aniline: 2,4,6-TMA (moles) | Feed Flow Rate ml/hr | N$_2$ Gas Flow ml/min | Reaction Temp (degrees) | Conversion of 2,4,6-TMA | Selectivity to 2,6-DMA | Selectivity to p-toluidine |
|---|---|---|---|---|---|---|---|---|
| 17 | 19% Cr$_2$O$_3$/Al$_2$O$_3$ | 1 | 2 | 40 | 500 | 51 | 17 | 31 |
|  |  | 2 | 3 | 10 | 450 | 26 | 10 | 30 |
| 18 | 24% ZnO/Al$_2$O$_3$ | 2 | 3 | 10 | 450 | 10 | 20 | 50 |
| 19 | 10% ZnO/10% Cr$_2$O$_3$/Al$_2$O$_3$ | 2 | 3 | 10 | 375 | 4 | 0 | 50 |
|  |  |  |  |  | 450 | 48 | 18 | 40 |
| 20 | 10% WO$_3$/Al$_2$O$_3$ | 2 | 3 | 10 | 375 | 22 | 68 | 54 |
|  |  |  |  |  | 450 | 56 | 38 | 52 |
| 21 | 10% V$_2$O$_5$/Al$_2$O$_3$ | 2 | 3 | 10 | 375 | 8 | 14 | 31 |
|  |  |  |  |  | 450 | 21 | 0 | 24 |
| 22 | 20% Fe$_2$O$_3$/Al$_2$O$_3$ | 2 | 3 | 10 | 375 | 5 | 0 | 100 |
|  |  |  |  |  | 450 | 17 | 26 | 48 |

TABLE II

| Example No. | Catalyst | Feed Ratio Aniline 2,4,6-TMA (moles) | Reaction Temp (degrees) | Reaction Time (hr) | Conversion of 2,4,6-TMA | Selectivity to 2,6-DMA | Selectivity to p-Toluidine |
|---|---|---|---|---|---|---|---|
| 23 | HY Zeolite | 2 | 350 | 2 | 71 | 94 | 76 |
|  |  |  | 375 | 2 | 75 | 86 | 62 |
|  |  |  | 350 | 4 | 69 | 91 | 75 |
|  |  |  | 350 | 8 | 76 | 89 | 65 |
|  |  |  | 375 | 1 | 70 | 88 | 71 |
| 24 | 91% Al$_2$O$_3$/6% SiO$_2$ (Amorphous) | 1 | 300 | 2 | 21 | 93 | 92 |
| 25 | 87% SiO$_2$/13% Al$_2$O$_3$ Amorphous | 1 | 300 | 2 | 12 | 93 | 100 |
| 26 | Sb/9Ti/O | 2 | 350 | 2 | 6 | 42 | 33 |

TABLE III

| Example No. | Feed Composition (mole %) o-Toluidine | 2,4-DMA | 2,6-DMA | Reaction Temp (degrees) | Product $\frac{2,6\text{-DMA} \times 100}{2,4\text{-DMA} + 2,6\text{-DMA}}$ (mole percent) |
|---|---|---|---|---|---|
| 27 | 52.7 | 43.4 | — | 296 | 1 |
|  |  |  |  | 308 | 2 |
|  |  |  |  | 338 | 5 |
|  |  |  |  | 340 | 16 |
|  |  |  |  | 350 | 8 |
|  |  |  |  | 393 | 18 |
| 28 | 42.6 | — | 55.9 | 290 | 85 |
|  |  |  |  | 306 | 50 |
|  |  |  |  | 325 | 47 |
|  |  |  |  | 334 | 49 |
|  |  |  |  | 348 | 52 |
|  |  |  |  | 365 | 50 |
| 29 | 47.9 | 22.3 | 29.8 | 282 | 55 |
|  |  |  |  | 321 | 49 |
|  |  |  |  | 349 | 45 |
|  |  |  |  | 368 | 43 |
|  |  |  |  | 387 | 43 |
|  |  |  |  | 406 | 47 |

EXAMPLES 30-31

2.4- and 2,6-DMA were equilibrated by reacting them with 2,4,6-TMA over HY zeolite catalyst using a procedure similar to that used for Examples 27-29. The results are summarized in Table IV.

EXAMPLES 32-34

Equilibration of 2,3-, 2,5-, and 3,4-DMA by reacting each with m-toluidine over the HY zeolite catalyst was carried out using a procedure similar to that described for Examples 27-29. The results are given in Table V. The product can also contain some aniline, o- and p-toluidine, and 2,4- and 2,6-DMA.

EXAMPLES 35-39

Equilibration of toluidines in the presence of HY zeolite was carried out in a manner similar to that used for Examples 27-29: 3 g of HY zeolite were used, the feed solution flow rate was 3 ml/hr in each case and the nitrogen flow rate was 10 ml/min. Results are summarized in Table VI. As can be seen from Example 35, the ortho and para isomers are nearly completely equilibrated before any appreciable amount of meta begins to form. Examples 37, 38 and 39 show the role played by aniline when HY catalyst is used as well as the importance of the disproportionation of toluidines to DMA's and aniline (Example 39). On the basis of beginning with p-toluidine/aniline and m-toluidine/aniline feeds, the three component equilibrium is approached as shown in FIG. 1. While a 10% solution of ortho-toluidine in aniline approaches the curve shown, a 1:1 mix of aniline and o-toluidine does not follow the curve, but bends toward the three component equilibrium much earlier. Pure o-toluidine proceeds almost straight to the three component equilibrium.

TABLE IV

| Example No. | Feed Composition (mole %) | | | Reaction Temp (degrees) | Product $\frac{2,6\text{-DMA} \times 100}{2,4\text{-DMA} + 2,6\text{-DMA}}$ (mole percent) |
| | 2,4,6-TMA | 2,4-DMA | 2,6-DMA | | |
|---|---|---|---|---|---|
| 30 | 48 | — | 52 | 252 | 96 |
| | | | | 273 | 95 |
| | | | | 310 | 79 |
| | | | | 340 | 38 |
| | | | | 363 | 37 |
| | | | | 405 | 40 |
| | | | | 435 | 46 |
| | | | | 471 | 51 |
| | | | | 502 | 68 |
| 31 | 44 | 56 | — | 290 | 7 |
| | | | | 318 | 19 |
| | | | | 355 | 28 |
| | | | | 387 | 33 |
| | | | | 423 | 27 |
| | | | | 467 | 30 |
| | | | | 501 | 25 |

TABLE V

| Example No. | Feed Composition | | Reaction Temp ° | Product Composition (mole %) | | | |
| | m-toluidine (mole %) | DMA (isomer/mole %) | | m-toluidine | 2,3-DMA | 3,4-DMA | 2,5-DMA |
|---|---|---|---|---|---|---|---|
| 32 | 53 | 2,3-DMA/46 | 293 | 53 | 46 | — | — |
| | | | 322 | 54 | 40 | 2.0 | 1.3 |
| | | | 346 | 57 | 35 | 2.8 | 2.4 |
| | | | 382 | 58 | 31 | 3.8 | 4.1 |
| | | | 420 | 56 | 21 | 4.8 | 7.4 |
| 33 | 52 | 3,4-DMA/44 | 282 | 61 | — | 39 | — |
| | | | 341 | 64 | 0.7 | 31 | 3.3 |
| | | | 371 | 64 | 1.3 | 27 | 6.4 |
| | | | 405 | 65 | 2.2 | 24 | 8.0 |
| | | | 438 | 62 | 5.3 | 16 | 11 |
| | | | 460 | 55 | 6.9 | 10 | 11 |
| | | | 483 | 50 | 7.8 | 8.8 | 9.4 |
| | | | 508 | 48 | 6.0 | 12 | 7.2 |
| 34 | 53 | 2,5-DMA/45 | 302 | 54 | 0.8 | — | 44 |
| | | | 320 | 57 | 1.1 | 4.7 | 36 |
| | | | 340 | 57 | 1.2 | 4.8 | 35 |
| | | | 363 | 57 | 4.6 | 4.9 | 31 |
| | | | 391 | 58 | 3.5 | 5.7 | 27 |
| | | | 403 | 56 | 5.2 | 6.3 | 23 |
| | | | 423 | 50 | 6.5 | 5.5 | 16 |
| | | | 453 | 45 | 6.9 | 4.8 | 14 |
| | | | 473 | 44 | 5.9 | 3.9 | 13 |

TABLE VI

| Example No. | Feed Composition (mole ratio) | Reaction Temp ° | Product Composition (mole %) | | | | | | |
| | | | Aniline | o-toluidine | p-toluidine | m-toluidine | 2,6-DMA | 2,4-DMA | 2,4,6-TMA |
|---|---|---|---|---|---|---|---|---|---|
| 35 | 0.3 o-toluidine: 0.7 p-toluidine: 1 aniline | 375 | 63 | 18 | 13 | 1.1 | 1.1 | 3.6 | 6.4 |
| | | 397 | 54 | 18 | 16 | 1.0 | 1.6 | — | — |
| | | 440 | 63 | 18 | 11 | 3.5 | 1.0 | 3.1 | 0.6 |
| | | 447 | 68 | 17 | 11 | 4.3 | 2.6 | 6.6 | — |
| | | 462 | 64 | 16 | 11 | 5.5 | 2.3 | 0.8 | 0.1 |
| | | 480 | 67 | 15 | 9.6 | 8.3 | — | — | — |
| | | 500 | 70 | 12 | 6.0 | 9.2 | 0.3 | 0.9 | 0.7 |
| 36 | 1 m-toluidine: 1 aniline | 290 | 52 | — | — | 46 | — | 1.4 | 0.2 |
| | | 320 | 53 | — | 0.1 | 46 | — | 0.4 | 0.1 |
| | | 354 | 53 | 0.3 | 0.3 | 46 | — | 0.3 | 0.2 |
| | | 407 | 52 | 0.9 | 0.8 | 46 | — | 0.5 | 0.3 |
| | | 454 | 54 | 3.0 | 2.1 | 39 | — | 0.9 | 0.5 |
| | | 500 | 59 | 5.3 | 3.6 | 30 | 0.3 | 0.9 | 0.6 |
| 37 | 1-o-toluidine: 1 aniline | 375 | 56 | 30 | 6.7 | 1.0 | 1.1 | 3.8 | 0.4 |
| | | 392 | 56 | 29 | 6.6 | 1.3 | 1.1 | 3.4 | 0.3 |
| | | 409 | 56 | 30 | 6.1 | 1.8 | 1.1 | 3.5 | — |
| | | 437 | 59 | 27 | 5.5 | 3.7 | 0.7 | 2.4 | 0.3 |
| | | 453 | 60 | 26 | 5.2 | 5.0 | 0.6 | 1.7 | 0.4 |
| | | 473 | 63 | 24 | 4.8 | 6.5 | — | 0.8 | — |
| 38 | .11-o-toluidine: | 317 | 88 | 11 | — | — | — | — | — |

TABLE VI-continued

| Example No. | Feed Composition (mole ratio) | Reaction Temp ° | Product Composition (mole %) | | | | | | |
|---|---|---|---|---|---|---|---|---|---|
| | | | Aniline | o-toluidine | p-toluidine | m-toluidine | 2,6-DMA | 2,4-DMA | 2,4,6-TMA |
| | .89 aniline | 357 | 88 | 9.3 | 1.5 | 0.2 | 0.1 | 0.1 | 0.2 |
| | | 402 | 88 | 7.1 | 2.9 | 0.5 | 0.2 | 0.2 | 0.3 |
| | | 415 | 90 | 9.1 | 0.7 | 0.2 | — | — | — |
| | | 423 | 90 | 6.9 | 2.4 | 0.5 | — | — | 0.5 |
| | | 444 | 90 | 6.2 | 2.2 | 0.8 | — | — | 0.4 |
| | | 451 | 90 | 6.9 | 1.4 | 0.8 | — | — | 0.3 |
| | | 468 | 91 | 5.3 | 1.8 | 1.3 | — | — | 0.3 |
| | | 489 | 92 | 3.9 | 1.3 | 1.8 | — | — | — |
| 39 | o-toluidine | 370 | 21 | 59 | — | — | 3.1 | 16 | 1.0 |
| | | 388 | 20 | 57 | 4.6 | 1.0 | 3.0 | 13 | 0.6 |
| | | 403 | 24 | 56 | — | — | 3.4 | 15 | 1.3 |
| | | 422 | 18 | 60 | 2.6 | 2.2 | 2.3 | 10 | 0.9 |
| | | 441 | 13 | 76 | 1.6 | 3.1 | 1.9 | 6.6 | 0.7 |
| | | 469 | 20 | 52 | 3.7 | 5.8 | 2.4 | 6.8 | 1.5 |
| | | 492 | 24 | 53 | 4.8 | 8.2 | 2.5 | 6.0 | 2.0 |

EXAMPLE 40-48

Equilibration of toluidines in the presence of other catalysts was conducted by using a procedure similar to that used for Examples 27-29: 3 g of catalyst were used, the feed solution flow rate was 2.2 ml/hr and the nitrogen flow rate was 10 ml/min. Results are shown in Table VII.

EXAMPLES 49-50

Equilibration of ethylanilines in the presence of HY zeolite was conducted by using a procedure similar to that used in Examples 27-29. A solution of aniline and either p-ethylaniline or o-ethylaniline was passed over 3 g of HY zeolite catalyst at atmospheric pressure and a given reaction temperature at a flow rate of 2.2 ml/hr with a nitrogen gas flow rate of 10 ml/min. The relative amounts of aniline and ethylanilines in the product are shown in Table VIII. There was also a small fraction of high-boiling unidentified material in the product.

TABLE VII

| Ex. No. | Catalyst | Feed Composition (mole ratio) | Reaction Temp (degrees) | Product Composition (mole %) | | | | | | |
|---|---|---|---|---|---|---|---|---|---|---|
| | | | | Aniline | o-toluidine | p-toluidine | m-toluidine | 2,6-DMA | 2,4-DMA | 2,4,6-TMA |
| 40 | (1) | 1 p-toluidine: 1 aniline | 300 | 75 | 12 | 8.0 | 2.4 | 0.4 | 0.3 | 0.7 |
| 41 | (2) | 1 p-toluidine: 1 aniline | 375 | 56 | — | 43 | — | 0.5 | — | — |
| | | | 500 | 68 | 6.0 | 22 | 1.0 | 2.0 | — | — |
| 42 | (3) | 1 p-toluidine: 1 aniline | 375 | 54 | — | 46 | — | — | — | — |
| | | | 500 | 66 | 4.3 | 26 | 0.3 | 2.4 | — | — |
| 43 | (4) | 1 p-toluidine: 1 aniline | 400 | 54 | — | 46 | — | — | — | — |
| | | | 500 | 65 | 2.9 | 29 | — | 2.2 | — | — |
| 44 | (5) | 1 p-toluidine: 1 aniline | 375 | 64 | 4.3 | 29 | 3.5 | — | — | — |
| | | | 500 | 51 | — | 49 | — | 0.5 | — | — |
| 45 | (6) | 1 p-toluidine: 1 aniline | 375 | 57 | 0.6 | 41 | — | 1.1 | — | — |
| | | | 500 | 65 | 1.5 | 32 | 0.6 | 0.9 | — | — |
| 46 | (7) | 1 o-toluidine: 2 aniline | 500 | 73 | 24 | 1.7 | 0.7 | 0.4 | 0.5 | — |
| | | | 500 | 79 | 18 | 1.6 | 0.6 | 0.2 | 0.4 | — |
| 47 | (8) | 1 o-toluidine: 2 aniline | 500 | 77 | 19 | 0.9 | 1.7 | 0.2 | 0.2 | — |
| 48 | (9) | 1 o-toluidine: 2 aniline | 500 | 82 | 15 | 1.0 | 0.9 | — | — | — |

(1) HY
(2) 91% Al$_2$O$_3$/6% SiO$_2$ (amorphous)
(3) 99% Al$_2$O$_3$
(4) 99% Al$_2$O$_3$
(5) 87% SiO$_2$/13% Al$_2$O$_3$
(6) 10% MoO$_3$/Al$_2$O$_3$
(7) 33% Cr$_2$O$_3$/Al$_2$O$_3$
(8) 10% MoO$_3$/SiO$_2$
(9) 10% V$_2$O$_5$/SiO$_2$ - containing Al$_2$O$_3$

TABLE VIII

| Example No. | Feed Composition (mole ratio) | Reaction Temp (degrees) | Product Composition (mole %) | | | |
|---|---|---|---|---|---|---|
| | | | Aniline | o-ethyl-aniline | p-theyl-aniline | m-ethyl-aniline |
| 49 | 1 p-ethyl-aniline: 1 aniline | 300 | 55 | 4.0 | 41 | — |
| | | 330 | 58 | 10 | 32 | — |
| | | 360 | 60 | 15 | 25 | — |
| | | 390 | 66 | 13 | 16 | 4.4 |
| | | 420 | 76 | 6.6 | 6.9 | 10 |
| 50 | 1 o-ethyl-aniline: 1 aniline | 275 | 46 | 53 | 0.6 | — |
| | | 300 | 49 | 49 | 1.9 | — |

TABLE VIII-continued

| Example No. | Feed Composition (mole ratio) | Reaction Temp (degrees) | Product Composition (mole %) | | | |
|---|---|---|---|---|---|---|
| | | | Aniline | o-ethyl-aniline | p-theyl-aniline | m-ethyl-aniline |
| | | 330 | 53 | 39 | 7.5 | — |
| | | 360 | 58 | 28 | 12 | 2.5 |
| | | 390 | 60 | 24 | 14 | 2.4 |
| | | 420 | 58 | 16 | 11 | 5.3 |

The invention being claimed is:

1. A process for interconverting 2,3-dimethylaniline, 2,5-dimethylaniline, and 3,4-dimethylaniline by transalkylation with m-toluidine, comprising contacting a mixture comprising one or more of 2,3-dimethylaniline, 2,5-dimethylaniline, and 3,4-dimethylaniline with m-toluidine in the presence of a strongly acidic alumina-silica catalyst at a temperature of from about 250° to about 525° C. and at a pressure of from about 10 kPa to about 10 MPa, with the proviso that where the catalyst is a zeolite it has pore dimensions of at least about 0.52 nm and has cages with dimensions greater than about 0.75 nm.

2. A process according to claim 1, conducted at a temperature from about 300° C. to about 500° C.

3. A process according to claim 2, wherein the catalyst is a type X or type Y zeolite.

4. A process according to claim 3, wherein the catalyst is a hydrogen-exchanged type Y zeolite.

* * * * *